United States Patent
Verard et al.

(10) Patent No.: US 10,456,594 B2
(45) Date of Patent: Oct. 29, 2019

(54) METHOD AND APPARATUS FOR BRACHYTHERAPY FEATURING TRACKING VIA SHAPE-SENSING

(75) Inventors: Laurent Verard, Eindhoven (NL); Luis Felipe Gutierrez, Jersey City, NJ (US); Dirk Binnekamp, Borne (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1370 days.

(21) Appl. No.: 13/519,201

(22) PCT Filed: Nov. 17, 2010

(86) PCT No.: PCT/IB2010/055239
§ 371 (c)(1),
(2), (4) Date: Oct. 4, 2012

(87) PCT Pub. No.: WO2011/080606
PCT Pub. Date: Jul. 7, 2011

(65) Prior Publication Data
US 2013/0204072 A1  Aug. 8, 2013

Related U.S. Application Data

(60) Provisional application No. 61/290,275, filed on Dec. 28, 2009.

(51) Int. Cl.
*A61N 5/10* (2006.01)
*A61B 5/06* (2006.01)
(Continued)

(52) U.S. Cl.
CPC ............ *A61N 5/1039* (2013.01); *A61B 5/055* (2013.01); *A61B 5/065* (2013.01); *A61B 6/032* (2013.01);
(Continued)

(58) Field of Classification Search
CPC .. A61N 2005/1024; A61N 5/10; A61N 5/103; A61N 5/1001; A61N 5/1002;
(Continued)

(56) References Cited

U.S. PATENT DOCUMENTS

| 5,800,333 A | 9/1998 | Lipre |
| 6,102,844 A | 8/2000 | Ravins et al. |

(Continued)

FOREIGN PATENT DOCUMENTS

| DE | 20106526 U1 | 8/2001 |
| WO | WO200113060 | 2/2001 |

(Continued)

OTHER PUBLICATIONS

Park, Y-L., Elayaperumal, S., Daniel, B.L., Kaye, E., Pauly, K.B., Black, R.J., Cutkosky, M.R., "MRI-compatible Haptics: Feasibility of using optical fiber Bragg grating strain-sensors to detect deflection of needles in an MRI environment," Proc. Intl. Soc. Mag. Reson. Med. 16 (2008), p. 282.*

(Continued)

*Primary Examiner* — Carrie R Dorna

(57) ABSTRACT

A brachytherapy method and apparatus include implanting an applicator having at least one radiation source or seed receiving channel (62) into soft tissue adjacent a target region (40) to be irradiated. A high resolution planning image (64) of the target region including the applicator is generated, wherein the high resolution planning image is used for determining a three-dimensional treatment plan (66). A position of the applicator is tracked relative to the target region (40) and the treatment plan (66). Tracking the position includes measuring, via shape-sensing, a location and shape of the at least one radiation source or seed receiving channel (62).

30 Claims, 10 Drawing Sheets

(51) Int. Cl.
*A61B 34/20* (2016.01)
*A61B 5/055* (2006.01)
*A61B 6/03* (2006.01)
*A61B 8/08* (2006.01)
*A61B 8/00* (2006.01)

(52) U.S. Cl.
CPC .............. *A61B 6/037* (2013.01); *A61B 8/483* (2013.01); *A61N 5/1014* (2013.01); *A61N 5/1027* (2013.01); *A61N 5/1048* (2013.01); *A61B 8/4245* (2013.01); *A61B 2034/2061* (2016.02); *A61N 2005/1008* (2013.01); *A61N 2005/1051* (2013.01); *A61N 2005/1058* (2013.01)

(58) Field of Classification Search
CPC ...... A61N 5/1007; A61N 5/1014–1017; A61N 5/1027; A61N 2005/1008; A61N 2005/1009; A61N 2005/1012; A61N 2005/1018; A61B 5/062; A61B 5/064; A61B 5/065; A61B 8/12; A61B 2019/5261; A61B 19/246; G01L 1/246; G02B 6/02076
USPC ................. 600/3, 7, 8, 407, 424; 385/10, 12
See application file for complete search history.

(56) References Cited

U.S. PATENT DOCUMENTS

| | | | |
|---|---|---|---|
| 6,129,670 A | 10/2000 | Burdette et al. | |
| 6,311,084 B1 * | 10/2001 | Cormack et al. | ............. 600/411 |
| 6,366,796 B1 | 4/2002 | Yanof et al. | |
| 6,458,068 B1 | 10/2002 | Ellard et al. | |
| 6,471,710 B1 * | 10/2002 | Bucholtz | ...................... 606/130 |
| 6,505,065 B1 | 1/2003 | Yanof et al. | |
| 6,868,195 B2 | 3/2005 | Fujita | |
| 7,229,401 B2 | 6/2007 | Kindlein | |
| 8,262,555 B2 | 9/2012 | Jervis et al. | |
| 8,529,872 B2 | 9/2013 | Frank et al. | |
| 8,721,514 B2 | 5/2014 | Shechter | |
| 2004/0228509 A1 | 11/2004 | Holupka et al. | |
| 2007/0129593 A1 | 6/2007 | Gueye et al. | |
| 2008/0154085 A1 * | 6/2008 | Jervis et al. | ..................... 600/3 |
| 2008/0285909 A1 * | 11/2008 | Younge | ................ A61B 5/1076 385/13 |
| 2012/0323117 A1 | 12/2012 | Neustadter et al. | |

FOREIGN PATENT DOCUMENTS

| | | |
|---|---|---|
| WO | 0216965 A2 | 2/2002 |
| WO | 0216965 A3 | 2/2002 |
| WO | 2007094001 A3 | 4/2008 |
| WO | WO2009053897 | 4/2009 |

OTHER PUBLICATIONS

Park, Y-L., et al. "MRI-compatible Haptics Feasibility of using optical fiber Bragg grating strain-sensors to detect deflection of needles in an MRI environment", Proc. Intl. Soc. Mag. Reson. Med 16 (2008), p. 282.

* cited by examiner

Ultrasound image

METHOD AND APPARATUS FOR BRACHYTHERAPY FEATURING TRACKING VIA SHAPE-SENSING

The present embodiments relate generally to medical systems and more particularly, to a method and apparatus for brachytherapy featuring tracking via shape-sensing.

The present application relates to the therapeutic arts. It finds particular application in conjunction with high dose rate (HDR) brachytherapy and will be described with particular reference thereto. However, it is to be appreciated that the embodiments of the present disclosure will also find application in conjunction with other therapeutic treatments, for example, low dose brachytherapy and positioning of other treatment sources. In addition, various examples presented herein relate to brachytherapy treatment of prostate cancer. However, the methods described herein are also applicable to treatment of organs beyond the prostate, including, for example, breast, lung, liver, uterus, cervix and other organs where similar therapy and improved workflow and patient care are desired.

Cancer is often treated with a combination of therapies, such as surgery, chemotherapy, radiation therapy, and the like. For example, a tumor is often removed surgically, after which the patient is treated with chemotherapy or radiation to kill any cancerous cells which were not removed. In one radiation treatment, a beam of x-rays from a linear accelerator is directed through a target region. By contrast, in brachytherapy, a seed is inserted into a target region to irradiate the target region from within.

In HDR brachytherapy, an applicator in the form of a catheter is positioned in the patient, extending through the target area to be irradiated. A high dose rate source (e.g., an iridium 192 pellet) or seed is moved through the catheter on the end of a wire and dwells at one or more preplanned positions for a planned period of time. This treatment is repeated, typically, once or twice per day over a period of several days.

HDR brachytherapy procedures depend upon delivering fractionated therapy doses to designated target volumes by timed insertion of a small (e.g., 2-4 mm long) seed radiation source of (e.g., Ir-192) into body cavities or tumors. The Ir-192 source is attached to a wire and pushed/pulled through previously surgically inserted catheters. Presently, HDR procedures rely on computer controlled mechanical delivery systems to track the location of the source in the body. While such a source tracking method is generally acceptable, in some cases there has been movement of the surgically inserted catheter between the time of insertion and the time of brachytherapy treatment resulting in mislocation of the seed source. Such movements may be due to organ motion, swelling, and catheter shift. The verification process of the catheter set location is implemented prior to every fraction today using x-ray and ultrasound imaging. Unfortunately this process is cumbersome, tedious, lengthy and costly. In extreme cases where undetected motion occurred, unintended exposure of the patient healthy tissues to such high radiation doses for an extended period of time can result in severe injury or death of the patient.

Thus, a device and method for the real time, in situ tracking of seed sources channels/applicators would be highly desirable to assure the proper location of a radiation source or seed during brachytherapy treatment.

Accordingly, an improved method and system for overcoming the problems in the art is desired.

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements.

FIG. 1 is a flow diagram view of a method of brachytherapy known in the art;

FIG. 2 a flow diagram view of a method of brachytherapy featuring tracking via shape-sensing according to an embodiment of the present disclosure;

Figure 7:
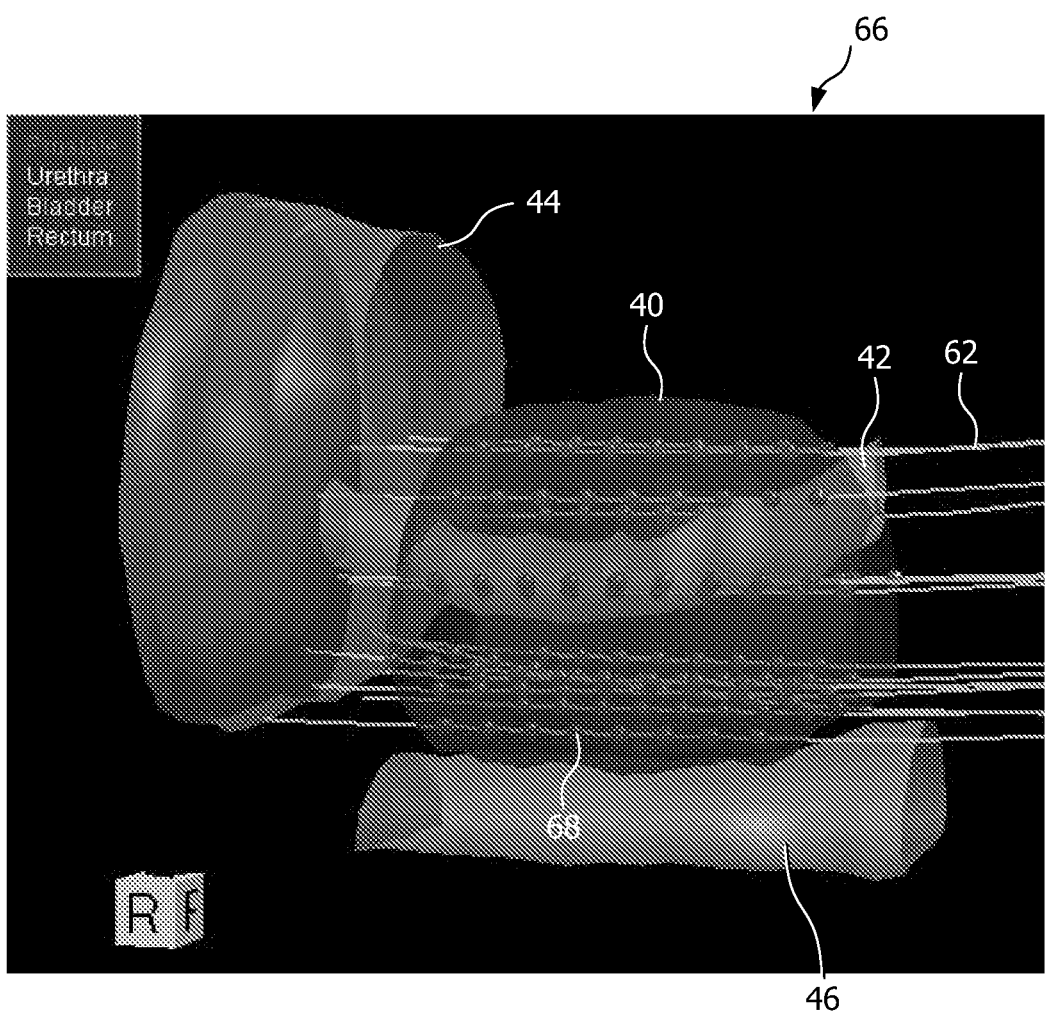
Figure 8:
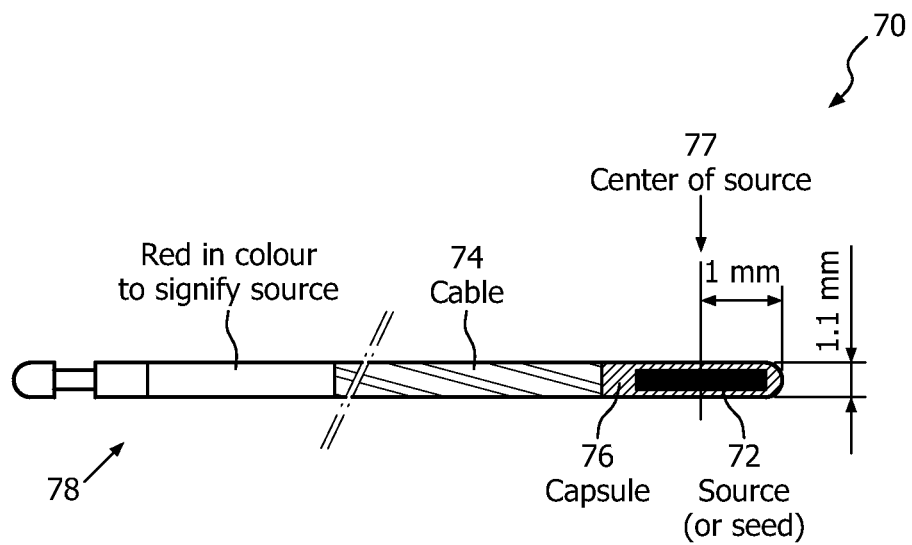
Figure 9:
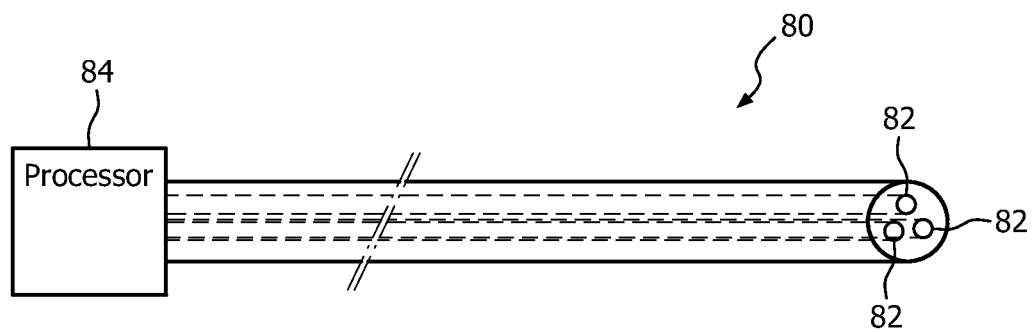
Figure 10:
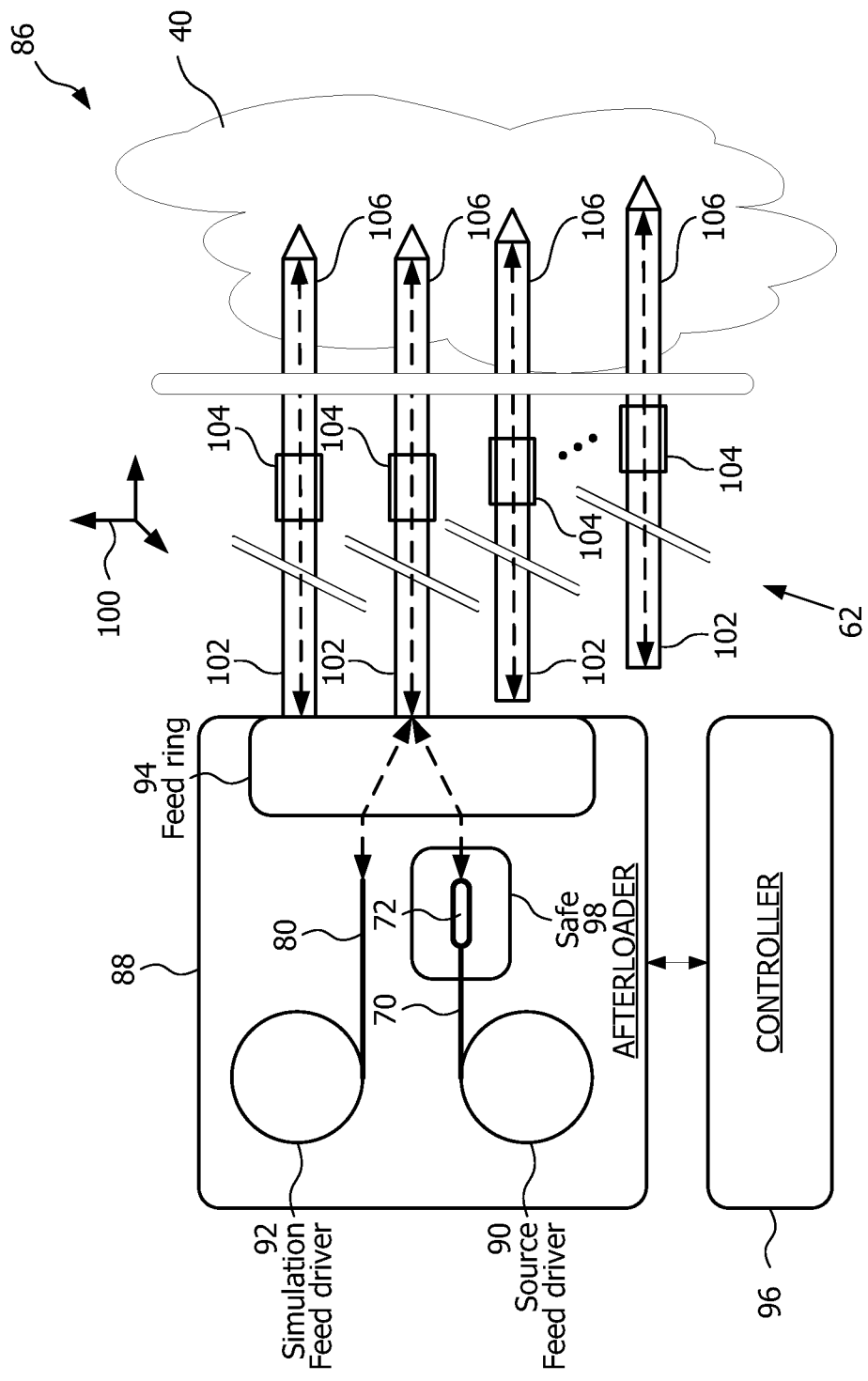
Figure 11:
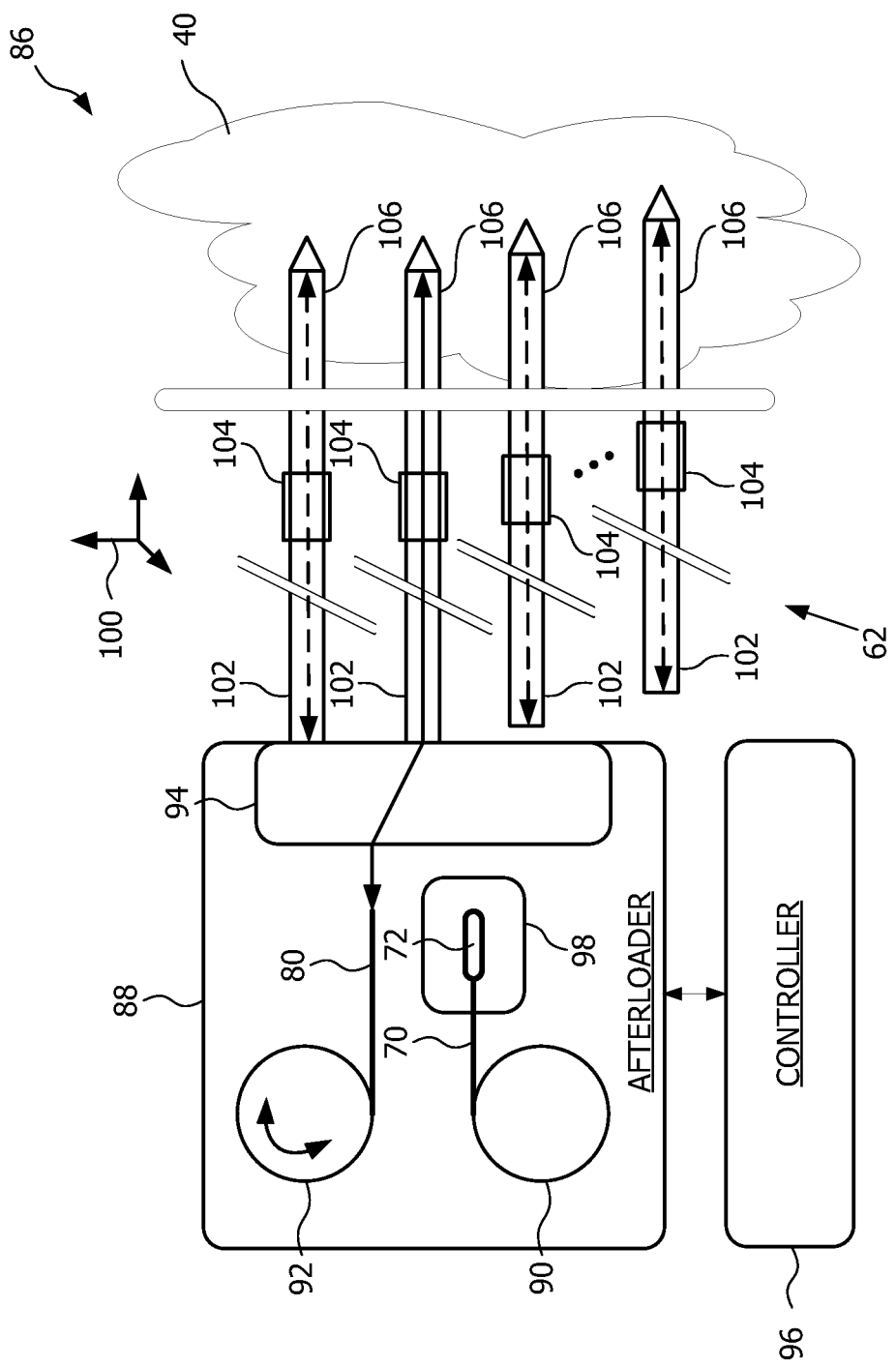
Figure 12:
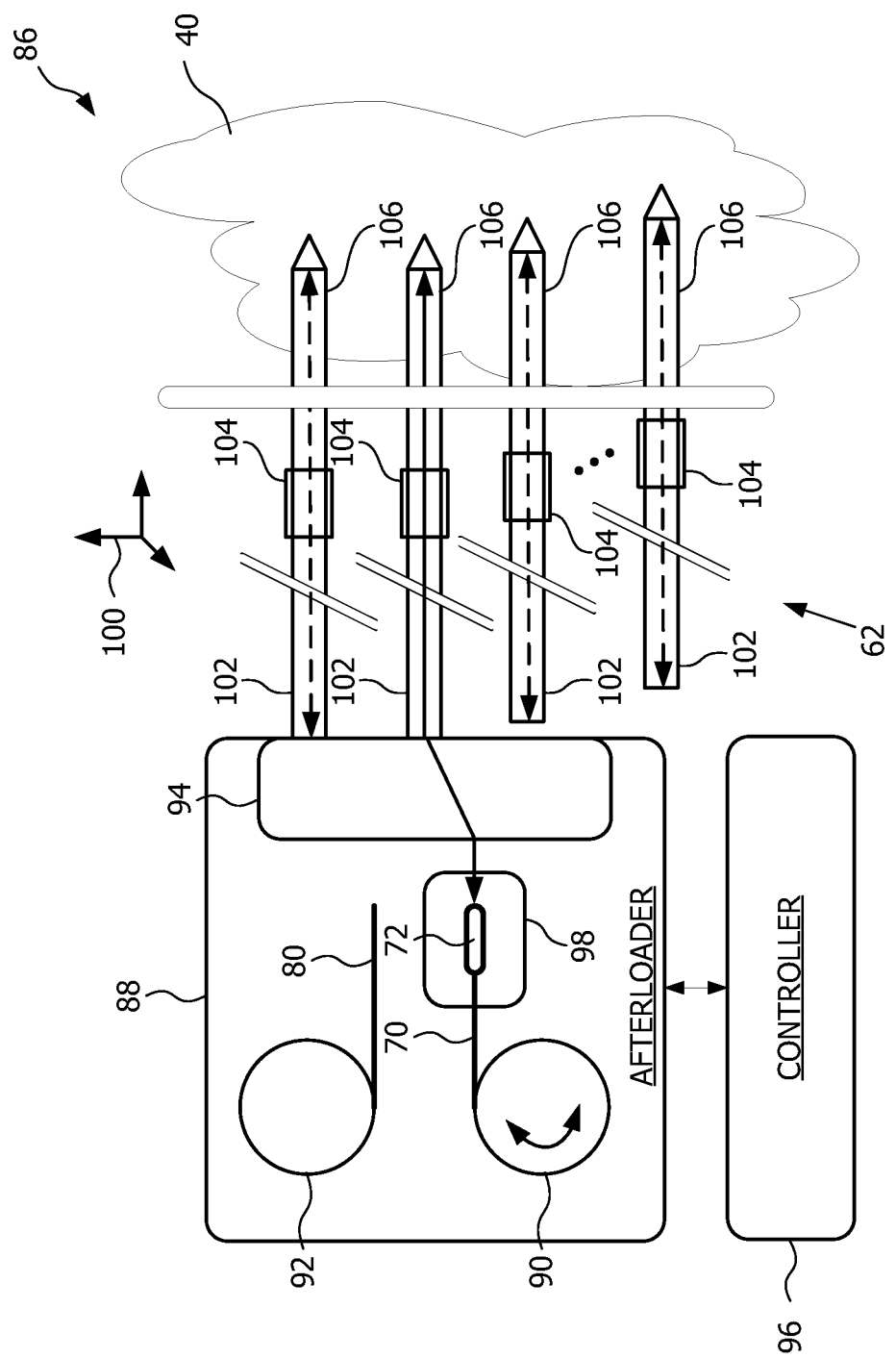

FIG. 7 is a three-dimensional perspective view of a volume showing a portion of the target region to be treated during brachytherapy treatment, and neighboring anatomy, wherein a number of planned treatment locations within the target region, and more particularly, a corresponding array of radiation source or seed receiving channels, with various dwell locations, are illustrated in the respective channels;

FIG. 8 is an illustrative view of a cable of a source feed device having a radiation source or seed coupled to a tip of the cable, for use in a brachytherapy method and apparatus according to one embodiment of the present disclosure;

FIG. 9 is an illustrative view of a Fiber Bragg Grating (FBG) optical cable for use in tracking a position of an applicator relative to a target region and treatment plan, wherein tracking the position includes measuring, via shape-sensing, a location and shape of at least one radiation source or seed receiving channel in a brachytherapy apparatus according to one embodiment of the present disclosure;

FIG. 10 is a block diagram view of a brachytherapy apparatus featuring tracking via shape-sensing according to an embodiment of the present disclosure;

FIG. 11 is a block diagram view of a brachytherapy apparatus featuring tracking via shape-sensing through at least one of deployment and retrieval of a simulation feed device according to one embodiment of the present disclosure; and FIG. 12 is a block diagram view of a brachytherapy apparatus featuring tracking via shape-sensing through at least one of deployment and retrieval of a source feed device according to one embodiment of the present disclosure.

As discussed herein, the embodiments of the present disclosure and the various features and advantageous details thereof are explained more fully with reference to the non-limiting examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. For example, optical shape sensing (OSS) with use of Fiber Bragg Grating (FBG) optical fibers is known in the art, and thus only briefly discussed herein. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law. Moreover, it is noted that like reference numerals represent similar parts throughout the several views of the drawings.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

As discussed herein, in brachytherapy, radioactive seeds or sources are preferably delivered exactly to a location dictated by a treatment plan. In order to do so, a set of metal needles is placed in the patient. These needles are then connected one after the other to flexible catheters that are linked to an afterloader. The afterloader then sends a radioactive source through the catheter and needle at the exact location programmed by the treatment plan.

Currently available afterloaders are limited to control and monitor of the length (i.e., depth) of a source along a one-axis catheter/needle construct. Current afterloader devices also provide poor, if any, control of the delivery location with respect to the anatomy and with respect to other locations where previous sources have been delivered. The embodiments of the present disclosure advantageously overcome the problems and limitations of the currently available afterloader devices. The embodiments of the present disclosure advantageously make brachytherapy easier, improve control and provide assurance that therapy is delivered according to plan.

One advantage of the embodiments of the present disclosure resides in a reduction of undesirable radiation exposure to healthy tissue during brachytherapy, and a greater accuracy of radiation to the desired treatment locations. In other words, the embodiments of the present disclosure provide for more assured accuracy in carrying out a planned brachytherapy. The embodiments of the present disclosure advantageously use Fiber Bragg Grating optical fiber(s) as an adjunct to existing afterloader devices, the FBG optical fiber(s) adapted to measure the location and shape of each catheter, and collect information about the entire set of catheters in 3D to ensure no significant motion occurred from one catheter to another. In one embodiment, a FBG optical fiber is deployed first, that is, as a "dummy" source by the afterloader, and retrieved. Once measurement is acquired (i.e., within seconds), the radioactive source, attached to a cable, is then deployed to the desired location for providing the desired treatment. In another embodiment, the cable of the radioactive source also comprises a FBG optical fiber, the FBG cable thus being used to track the radioactive source as well during a brachytherapy treatment.

According to the embodiments of the present disclosure, Fiber Bragg Grating technology advantageously provides for real-time localization (<1 mm) and strain information of the flexible catheters utilized during HDR brachytherapy delivery fractions. The FBG optical fibers advantageously provide a simple, fast and accurate way to verify and monitor the entire shape of implanted catheters prior to and during radiation delivery of brachytherapy treatment. In addition, FBG optical fiber size, flexibility, and form factor render FBG optical fibers very well suited for use in an afterloader and in catheters. Furthermore, FBG optical fibers are immune to environmental metallic conditions (as compared to electromagnetics). Moreover, active source cable of an afterloader device is on the order of 0.7 mm outer diameter. An FBG optical fiber is on the order of 0.4 mm outer diameter, and thus would fit well into an afterloader.

In one embodiment, a brachytherapy apparatus and method uses shape-sensing built into an afterloader. The shape sensing detects in real-time tip location and shape in 3D of applicators/needles or catheters, as well as, radiation sources/seeds within needles and catheters, used in the delivery of a radiation treatment. The information on tip location and needle and catheter shape is used to control and adapt planning or delivery of treatment to assure optimal control of the location(s) to which radiation is delivered. A fiber optic shape sensor is well suited for this application because it can easily be built inside and be driven by the afterloader. The radiation source may be designed to be attached to the fiber as a replacement of an existing cable/guidewire or be a "dummy source" based on the fiber to simulate the delivery just before the real source delivery.

In operation, as the active source is being delivered inside the body to the target site at the pre-planned location and dwell parameters, a real-time assessment of the position, shape, and radiation dose measurements can be transmitted back to the controller or control station. In the event that the local anatomical and functional environment of the target site changes, and can be assessed compared to the pre-existing plan, a planning workstation takes the new information into account and re-calculate in real-time and/or when necessary the dose distribution accordingly in 3D. When the active source is being deployed in the current channel and/or next channels, the dose distribution plans are being monitored and modified as required for a more accurate radiation therapy and reduced side effects to healthy tissues surrounding and/or neighboring the prostate (e.g., urethra, nerves, blood vessels, sphincter, rectum, and bladder).

According to yet another embodiment, an FBG optical fiber is used as a means to represent the 3D shape of the urethra during image acquisition to help with planning and dose delivery. It is noted that the urethra is a critical component/organ for this procedure and is somewhat difficult to identify with conventional imaging.

In another embodiment, the brachytherapy method includes using a 3D shape-sensing optical fiber to provide a means to help co-register multiple imaging modalities with an in-situ registration. For example, an FBG optical fiber is inserted inside the urethra during CT, MR, PET or 3D angio, and the 3D shape of the urethra can be used to match the 3D urethra (i) for planning (thus, merging several imaging modalities) and (ii) during intervention with 3D ultrasound, for example.

Figure 1:
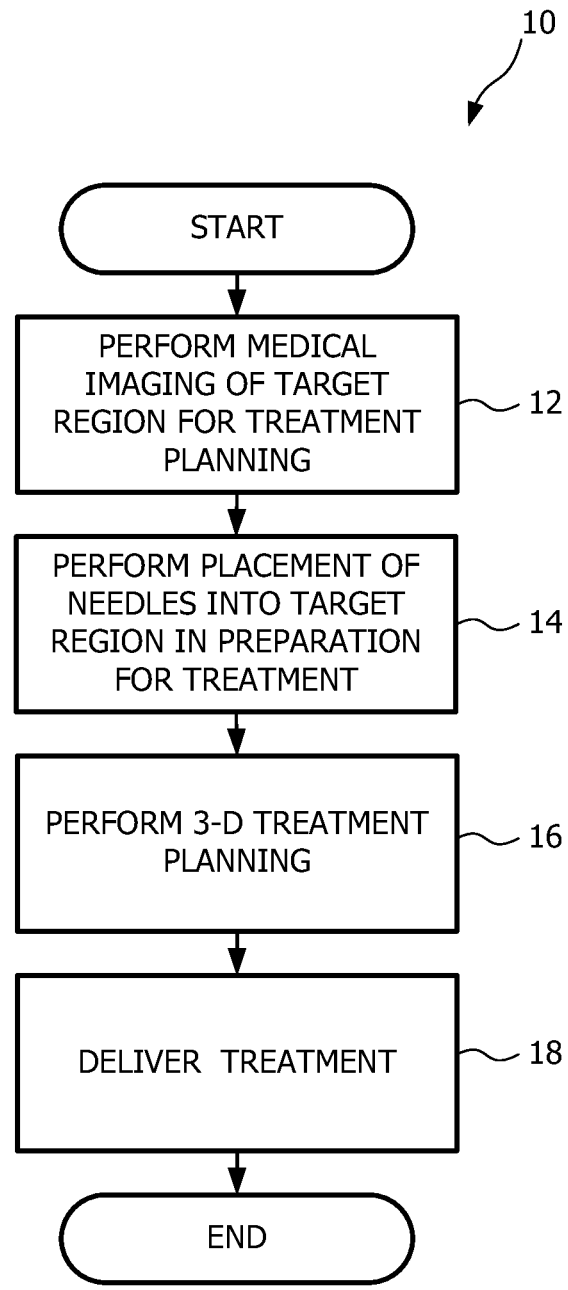

Referring now to FIG. 1, a flow diagram view is shown of a brachytherapy method 10 known in the art. The method begins with the performing of medical imaging of a target region for treatment planning, as indicated by reference numeral 12. Subsequent to performing the medical imaging, the method includes placement of needles into the target region in preparation for the brachytherapy treatment, indicated by reference numeral 14. Upon placement of the needles, 3-D treatment planning is performed, as indicated by reference numeral 16. Treatment is then delivered at 18, and thereafter the method ends. The particulars of the work flow of the brachytherapy method depend upon the target anatomy and related radiation distribution. In addition, the work flow may differ from one anatomy to another.

Figure 2:
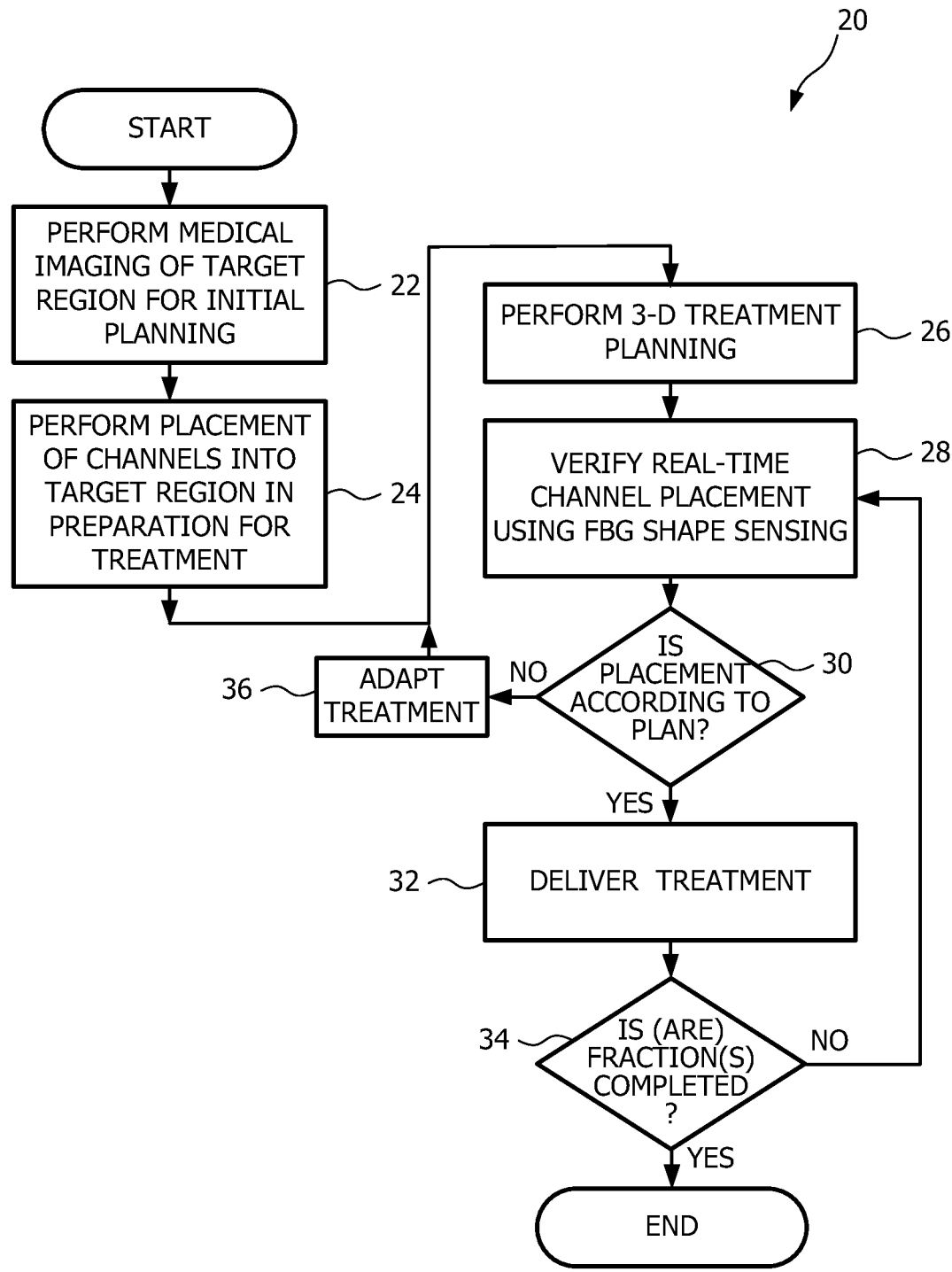

FIG. 2 a flow diagram view of a brachytherapy method 20 featuring tracking via shape-sensing according to an embodiment of the present disclosure. The method begins with the performing of medical imaging of a target region for treatment planning, as indicated by reference numeral 22. Subsequent to performing the medical imaging, the method includes placement of channels into the target region in preparation for the brachytherapy treatment, indicated by reference numeral 24. As will be discussed further herein, the channels being placed can include one or more of catheters, connectors, and needles of an applicator, configured for a given anatomy and brachytherapy treatment. Upon placement of the channels, 3-D treatment planning is performed, as indicated by reference numeral 26. Subsequent to performing the 3-D treatment planning, the method includes verifying a real-time channel placement using FBG shape sensing, as indicated by reference numeral 28. A query is then conducted to determine whether placement is according to the 3-D treatment plan, as indicated by reference numeral 30. If the placement is according to the 3-D treatment plan within a threshold amount, then the method proceeds with delivering treatment, as indicated by reference numeral 32. Upon completion of the delivered treatment, a query is conducted as to whether a given treatment fraction is completed (or all treatment fractions for a given brachytherapy treatment are completed), as indicated by reference numeral 34. Assuming that the given treatment fraction is completed (or that all treatment fractions for the given brachytherapy treatment are completed), then the method ends. On the other hand, if the given treatment fraction is not yet completed, then according to one embodiment, the method returns to step 28 with the verifying of real-time channel placement using FBG shape sensing. The method then continues with the query at step 30. Referring again to step 30, if the query of whether placement of the channels is according to plan results in the placement of the channels not being within a threshold amount, then the method proceeds to step 36. In step 36, the treatment (or treatment plan) is adapted as a function of the misplacement of the channels. The method next proceeds again to step 26 with the performance of 3-D treatment planning; however, in this instance, the performance of 3-D treatment planning takes into account the adaptation of the treatment as a function of the misplacement of the channels. Accordingly, the method advantageously provides verification of channel placement in real-time, not only prior to a treatment delivery, but also during a treatment delivery. In addition, verification of channel placement is advantageously provided for a single treatment fraction, and over a number of treatment fractions.

Figure 3:
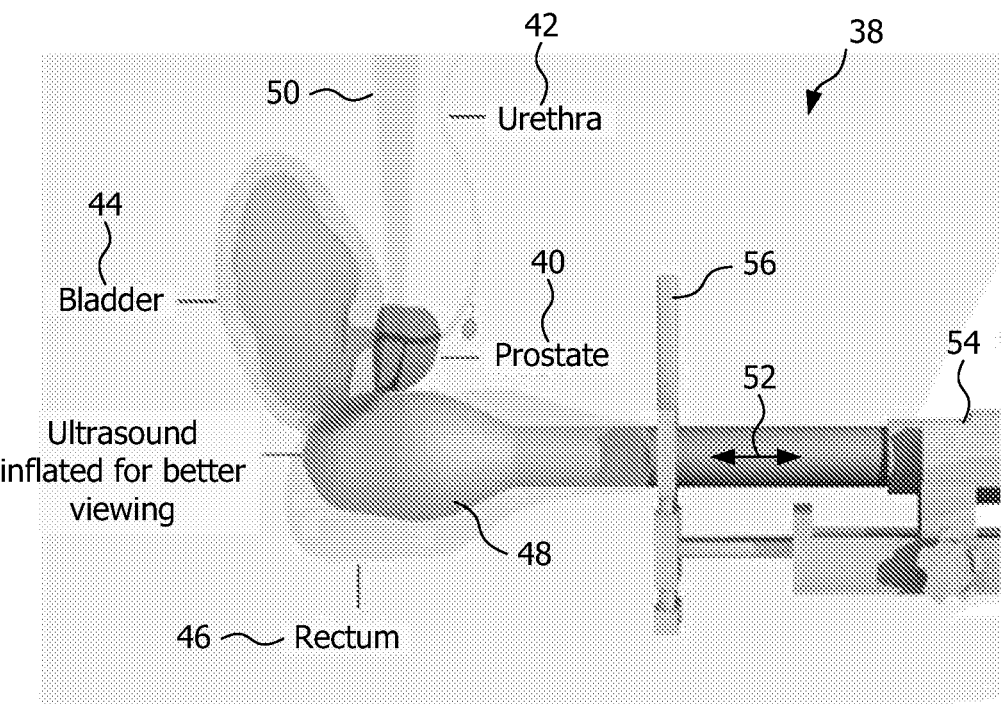
FIG. 3 is side perspective, schematic representation view of a target region to be irradiated during brachytherapy treatment, a neighboring anatomy, an ultrasound probe, and a template for use in accordance with the embodiment of the present disclosure.

FIG. 3 is side perspective, schematic representation view 38 of a target region to be irradiated during brachytherapy treatment, a neighboring anatomy, an ultrasound probe, and a template for use in accordance with the embodiment of the present disclosure. In this illustration, the target anatomy 40 represents a prostate. The neighboring anatomy includes portions of anatomy proximate to the target anatomy. For example, the neighboring anatomy includes the urethra 42, the bladder 44, and the rectum 46. The ultrasound probe 48 is shown as being inserted within the rectum 46 and in close proximity to the prostate 40. The ultrasound probe 48 is configured to generate one or more ultrasound beam, such as indicated by reference numeral 50, before and/or during a treatment delivery of the brachytherapy procedure. The ultrasound probe 48 is used for obtaining one or more ultrasound images (FIG. 4) of the target region or anatomy 40.

Figure 4:
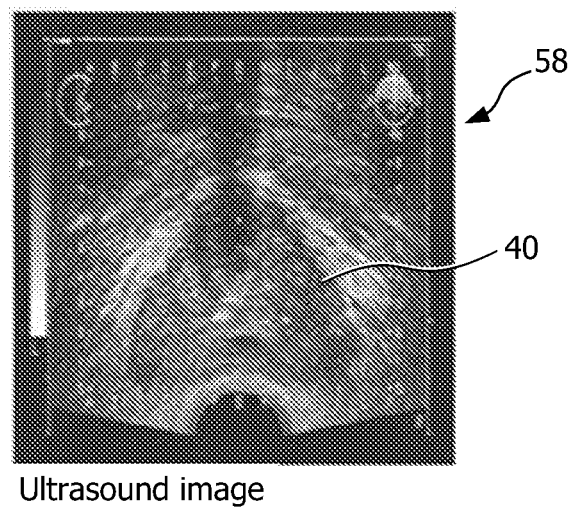
FIG. 4 is an illustrative view of a slice of an ultrasound image, showing a portion of the target region to be treated during brachytherapy treatment and neighboring anatomy.

Referring still to FIG. 3, the ultrasound probe 48 is configured for being displaced or moved with respect to the target region 40, for example, in a direction as indicated by arrow 52. Movement of the ultrasound probe 48 is carried out, for example, by use of a suitable stepper motor 54. In addition, a template 56 for use in the placement of an applicator with respect to the target region 40 is coupled with respect to the ultrasound probe, via suitable coupling means, wherein a registration between the template (and subsequently the applicator) can be readily determined with reference to the ultrasound probe. In other words, appropriate registration between the imaging system of the ultrasound probe 48 and that of tracking a position of the applicator relative to the target region 40 and a treatment plan, as will be discussed herein below, can be obtained. FIG. 4 is an illustrative view of a two-dimensional slice of an ultrasound image 58, showing a portion of the target region 40 to be treated during brachytherapy treatment and the neighboring anatomy.

Figure 5:
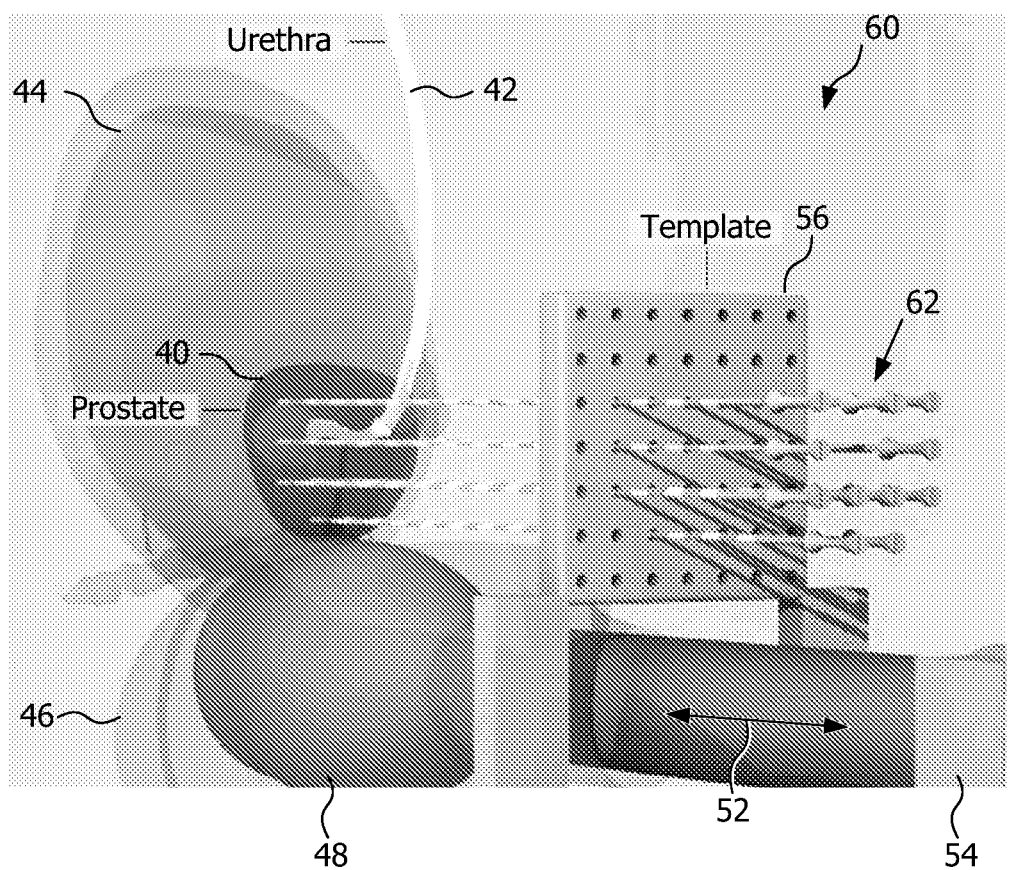
FIG. 5 is a three-dimensional, schematic representation, view of the target region to be irradiated during brachytherapy treatment, neighboring anatomy, ultrasound probe, template, and an array of radiation source or seed receiving channels for use in accordance with one embodiment of the present disclosure.

FIG. 5 is a three-dimensional, schematic representation, view of the target region 40 to be irradiated during brachytherapy treatment, neighboring anatomy (42,44,46), ultrasound probe 48, template 56, and an array of radiation source or seed receiving channels 62 for use in accordance with one embodiment of the present disclosure. In one embodiment, the array of radiation source or seed receiving channels 62 comprises an applicator. Accordingly, the applicator has at least one radiation source or seed receiving channel to be implanted in soft tissue adjacent a target region 40 to be irradiated, as will be discussed further herein with reference to FIGS. 10-12. As used herein, the phrase "implanted adjacent the target region" 40 can also be interpreted to include being implanted within the target region, since some portions or tissue of the target region may be irradiated, while other portions or tissue of the target region are not irradiated. This understanding should become clearer upon a reading of the discussion with reference to FIGS. 6 and 7.

Figure 6:
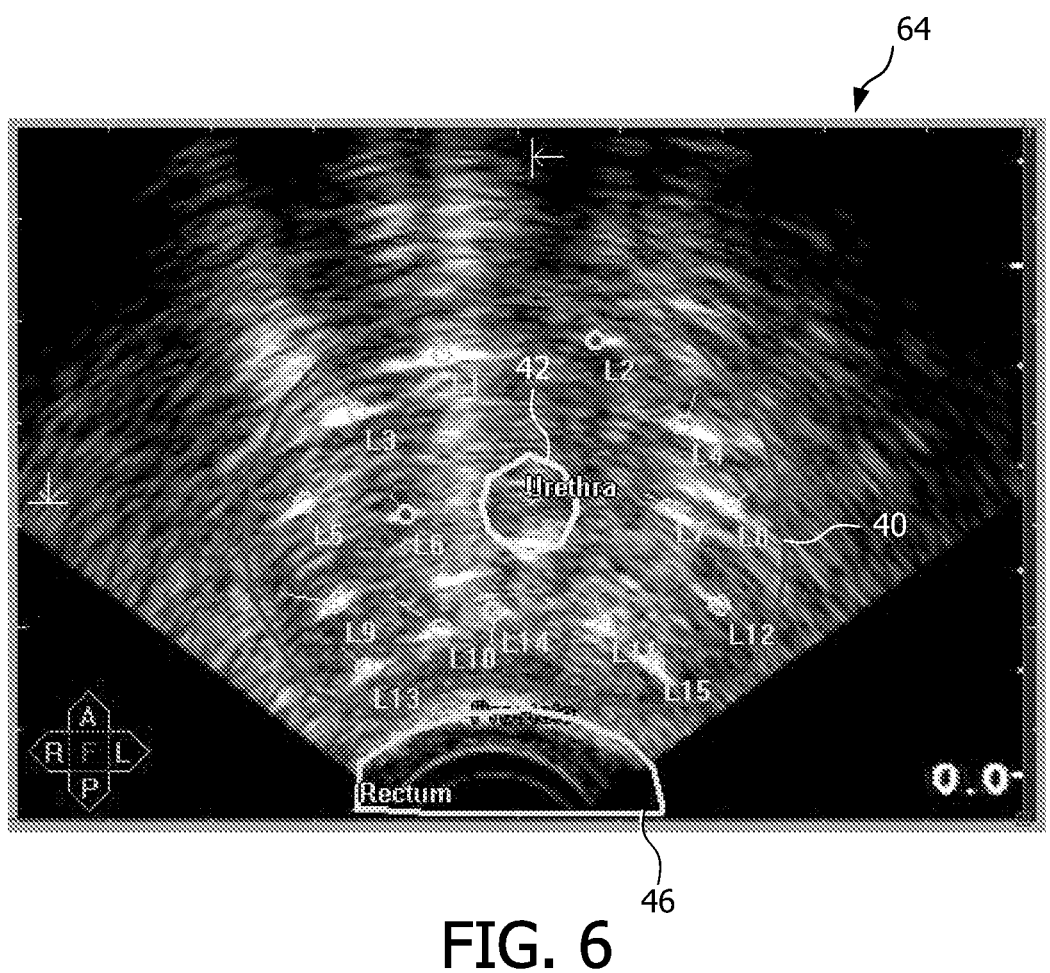
FIG. 6 is an illustrative view of a slice of an ultrasound image, showing a portion of the target region to be treated during brachytherapy treatment, a number of planned treatment locations within the target region, and neighboring anatomy.

FIG. 6 is an illustrative view 64 of a two-dimensional (2-D) slice of an ultrasound image, showing a portion of the target region 40 to be treated during brachytherapy treatment, a number of planned treatment locations within the target region, and neighboring anatomy. In this 2-D view 64, the neighboring anatomy which is discernable includes the urethra 42 and the rectum 46. Within this 2-D view 64, the target region 40 includes a number of treatment locations indicated by circles with the reference designations of L1, L2, . . . , L15. Within the target region, the number of treatment locations is a function of the number of sites within the three-dimensional volume of the target region diagnosed as being harmful (e.g., cancer).

FIG. 7 is a three-dimensional perspective view 66 of a volume showing a portion of the target region 40 to be treated during brachytherapy treatment, and neighboring anatomy (42,44,46), wherein a number of planned treatment locations within the target region, and more particularly, a corresponding array of radiation source or seed receiving channels 62, with various dwell locations, are illustrated in the respective channels. Only one of the dwell locations is identified, via reference numeral 68, for simplicity. As can be understood from FIG. 7, each channel of the array of radiation source or seed receiving channels 62 can include a number of dwell locations 68, corresponding to one or more locations 68 along a radiation source or seed receiving channel 62 at which a radiation source is held, stopped, or disposed for a given duration of time to provide a desired local radiation treatment to tissue within the target region 40, further as determined according to a given treatment plan. Note that the ultrasound probe 48 shown in FIGS. 3 and 5 can be traversed along the target region (arrow 52) while acquiring a series of 2-D ultrasound images, wherein the series of 2-D ultrasound images can be used in creating the view of the 3-D volume of the target region.

FIG. 8 is an illustrative view of a cable of a source feed device, generally indicated by reference numeral 70, having a radiation source or seed 72 coupled to a tip of the cable, for use in a brachytherapy method and apparatus according to one embodiment of the present disclosure. In one embodiment, a cable portion 74 of cable 70 comprises stainless steel. In another embodiment, the cable portion 74 comprises a FBG optical fiber, as will be discussed further herein. At a distal end or tip of the cable portion 74, a capsule 76 containing the source (or seed) 72 is securely coupled to the cable. At the opposite, proximate end, generally indicated by reference numeral 78, the cable 70 includes a suitable end configuration for use with a source feed device of an afterloader, as will be discussed further herein. The cable end 78 may include a colored end (for example, red), suitable for use in identifying cable 70 as a radiation source cable. In addition, in one example, the capsule 76 has an outer-diameter on the order of 1.1 mm and the source 72 is centered (indicated by reference numeral 77) within the capsule 76 at a location on the order of 1 mm. The overall length of cable 70 is determined according to the requirements of a given brachytherapy application or implementation.

FIG. 9 is an illustrative view of a Fiber Bragg Grating (FBG) optical cable 80 for use in tracking a position of an applicator relative to a target region and treatment plan, wherein tracking the position includes measuring, via shape-sensing, a location and shape of at least one radiation source or seed receiving channel in a brachytherapy apparatus according to one embodiment of the present disclosure. The FBG optical cable 80 of FIG. 9 includes a three-channel FBG optical cable, each channel being indicated by reference numeral 82. The FBG optical cable 80 could also be one of a one-channel, a two-channel, or a four-channel FBG optical cable. In addition, the embodiments of the present disclosure can include one or more FBG optical cables, wherein the one or more FBG optical cables may further include one or more one-channel, two-channel, three-channel, four-channel, or various combinations thereof. Illustrated with the FBG cable 80 is a processor 84 for measuring, via shape-sensing, a location and shape of the corresponding FBG optical cable. The overall length of FBG optical cable 80 is determined according to the requirements of a given brachytherapy application or implementation.

FIG. 10 is a block diagram view of a brachytherapy apparatus 86 featuring tracking via shape-sensing according to an embodiment of the present disclosure. Brachytherapy apparatus 86 includes a delivery device 88, for example, an afterloader device. The delivery device 88 includes a source feed drive or device 90, a simulation feed drive or device 92, and a feed ring 94. A controller 96 is coupled with the delivery device 88, wherein the controller comprises a suitably programmed processor, computer, or controller configured for implementing and/or for carrying out the various functions and process steps as described herein. The controller 96 may be integral with or separate from the delivery device 88.

Source feed drive 90 is coupled to and includes cable 70 having a radiation source or seed 72 coupled to a tip of the cable. Source feed drive 90 is controlled by controller 96 for deploying into and/or retrieving from a given channel of the array of channels 62, cable 70 having the source or seed 72. When not being used for radiation treatment, the source or seed 72 is retained within a safe 98, located within the delivery device 88. Simulation feed drive 92 is coupled to and includes a Fiber Bragg Grating optical cable 80. Simulation feed drive 92 is controlled by controller 96 for deploying into and/or retrieving from a given channel of the array of channels 62, FBG optical cable 80. In addition, feed ring 94 comprises, for example, a rotatable ring having apertures therein for redirecting one or more feed cable or source cable from a corresponding simulation or source feed drive into a desired one or more channels of the array of channels 62. Rotation of the feed ring 94 for routing of a given feed or source cable is controlled by controller 96. Controller 96 controls feed ring 94 for directing either one of a source cable 70 and/or a FBG optical cable 80 into one or more channels of the array of channels 62, according to the particulars of a given brachytherapy treatment.

To provide a clearer understanding of the array of channels 62 being arranged in three-dimensional space, a coordinate symbol 100 has been provided in FIG. 10. The array of channels 62 can include one or more of catheters 102, connectors 104, and needles 106 of an applicator, configured for a given anatomy and brachytherapy treatment. Connectors 104 couple catheters 102 to corresponding needles 106. Needles 106 are implanted within the soft tissue of the target region 40.

FIG. 11 is a block diagram view of a brachytherapy apparatus 86 featuring tracking via shape-sensing through at least one of deployment and retrieval of a simulation feed device according to one embodiment of the present disclosure. As discussed herein above, controller 96 is configured to control simulation feed drive 92 to operate by rotating the simulation feed drive for deploying into and/or retrieving from a given channel of the array of channels 62, the FBG optical fiber cable 80. In addition, controller 96 is configured to control feed ring 94 so as to route the FBG optical fiber cable 80 to a desired one of the array of channels 62 for tracking a position. Tracking the position includes measuring, via shape-sensing, a location and shape of the at least one radiation source or seed receiving channel according to the particulars of a given brachytherapy treatment. Measuring, via shape-sensing, can be carried out via processor 84 of FIG. 9 and/or in conjunction with controller 96. That is, processor 84 for measuring, via shape-sensing, a location and shape of the corresponding FBG optical cable may be incorporated within controller 96 or be separate from controller 96.

FIG. 12 is a block diagram view of a brachytherapy apparatus featuring tracking via shape-sensing through at least one of deployment and retrieval of a source feed device according to one embodiment of the present disclosure. As discuss herein above, controller 96 is configured to control source feed drive 90 to operate by rotating the source feed drive for deploying into and/or retrieving from a given channel of the array of channels 62, the source cable 70. In addition, controller 96 is configured to control feed ring 94 so as to route the source cable 70 to a desired one of the array of channels 62. As a result, the source 72 is deployed into at least one radiation source or seed receiving channel according to the particulars of a given brachytherapy treatment. In an alternate embodiment, the cable 72 includes a FBG optical cable, as discussed herein. In the later embodiment, the cable 72 that includes the FBG optical cable enables tracking a position of the source. Tracking the position includes measuring, via shape-sensing, a location and shape of the at least one radiation source or seed, as well as a location and shape of the at least one radiation source or seed receiving channel according to the particulars of a given brachytherapy treatment. Measuring, via shape-sensing, can be carried out via a processor similar to processor 84 of FIG. 9 and/or in conjunction with controller 96.

In operation, the delivery device (or afterloader) 88 is programmed with a planned brachytherapy session, loaded with cables 70, a radioactive pellet/source(s) 72 in pre-defined positions (so called dwell positions), and attached to a loading end of an applicator of channels 62. Thereafter, the afterloader moves the source through each of the selected catheters 102 to each of calculated locations (68, FIG. 7) for each of calculated durations. Again, brachytherapy sessions or fractions are typically administered one, two, or a few times a day for several days, e.g., 1-2 weeks. Between brachytherapy sessions, the applicator remains implanted. An alignment confirmation/readjustment procedure is performed prior to each brachytherapy session. When the next brachytherapy session is to commence, measuring via shape-sensing, a location and shape of a corresponding channel via an FBG optical fiber is used to localize or determine the position and orientation of the applicator, specifically the applicator on the patient. The relative locations of the applicator and the patient on a planning image stored in a planning image memory are compared by controller/processor 96 with current relative locations of the applicator in the planning image. If the relative positions have not changed beyond a threshold amount, indicating that the applicator has not changed orientation or location relative to the soft tissue, the afterloader 64 is reconnected and the next brachytherapy session is commenced.

However, if controller/processor 96 determines that the positions have changed, then one option is to attempt to reposition the applicator as additional measurements of a location and shape of the corresponding FBG optical fiber and channel are taken, trying to bring the applicator back or as close as possible to its original position and orientation. If the applicator is not in the original position at which the therapy was planned, a transform is determined by processor 96 between a current position and original position of the applicator, hence the surrounding (or neighboring) tissue and the target area. This transform is used by an image transforming process within processor 96 to operate on the planning image from a planning image memory to shift the relative location of the applicator and the target region in accordance with the transform to form a transformed therapy planning image. This shifted information is fed to an automatic therapy planning process of processor 96 to generate an adapted brachytherapy plan. The adapted brachytherapy plan is loaded into the afterloader 88 and the next brachytherapy session is commenced.

In one brachytherapy adapting planning embodiment, the applicator is implanted, a diagnostic 3D image set is generated, and a dose plan is created. During the dose delivery, the applicator and/or the radioactive pellet are tracked and a delivered dose is computed. For example, the target tissue could be divided into a 3D matrix of subregions. By mapping the tracked source location into the 3D matrix, the cumulative dose in each subregion can be continuously or intermittently updated or incremented based on time and distance from the source. The delivered dose can be monitored by computer and/or clinician. If a deviation from the dose plan is detected, an updated dose plan is generated. In addition, an optical fiber may be used to measure radiation dose. In other words, FBG fiber may serve the purpose of closing the loop for adaptive planning.

By now it should be appreciated that there has been provided a brachytherapy method according to one embodiment comprising: implanting an applicator having at least one radiation source or seed receiving channel in soft tissue adjacent a target region to be irradiated; generating a high resolution planning image of the target region including the applicator, the high resolution planning image for use in determining a three-dimensional treatment plan; and tracking a position of the applicator relative to the target region and the treatment plan, wherein tracking the position includes measuring, via shape-sensing, a location and shape of the at least one radiation source or seed receiving channel. In addition, in one embodiment, generating the high resolution planning image comprises using one or more selected from the group consisting of ultrasound, CT, MRI, X-ray, PET, and other medical imaging. Furthermore, in another embodiment, determining the three-dimensional treatment plan includes generating a radiation dose distribution map. Moreover, in yet another embodiment, tracking further includes measuring, via shape-sensing, using a fiber optic sensing device based on (i) Fiber Bragg Grating or (ii) Rayleigh scattering, or a combination thereof.

In another embodiment, the method further comprises at least one selected from the group consisting of (i) deploying at least one radiation source or seed into the target region via the at least one radiation source or seed channel and (ii) retrieving the at least one radiation source or seed out of the target region via the at least one radiation source or seed channel. The at least one radiation source or seed traverses the channel within the target region according to the treatment plan. In one embodiment, tracking the position may include at least one selected from the group consisting of (i) deploying a Fiber Bragg Grating optical fiber into the target region and (ii) retrieving the Fiber Bragg Grating optical fiber out of the target region via the at least one radiation source or seed channel. Tracking the position also includes acquiring measured location and shape information of the at least one radiation source or seed receiving channel via the Fiber Bragg Grating optical fiber.

In another embodiment, the deploying and retrieving of the at least one radiation source or seed into and out of the target region via the at least one radiation source or seed channel includes using a delivery device configured to deploy and retrieve the at least one radiation source or seed into and out of the target region via the at least one radiation source or seed channel. The delivery device comprises one or more source feed device, wherein the one or more source feed device includes a cable having a radiation source or seed coupled to a tip of the cable.

In yet another embodiment, the delivery device further comprises one or more simulation feed device, the one or more simulation feed device including at least one Fiber Bragg Grating optical cable, wherein the Fiber Bragg Grating optical cable is configured to implement the measuring, via shape-sensing, a location and shape of the at least one radiation source or seed receiving channel in response to (i) being deployed into the at least one radiation source or seed receiving channel to at least the target region and/or (ii) being retrieved out of the at least one radiation source or seed receiving channel from at least the target region. In a further embodiment, the at least one radiation source or seed receiving channel comprises an array of channels, the one or more simulation feed device comprises a plurality of simulation feed devices, still further wherein the plurality of simulation feed devices are deployed into and retrieved out of the array of channels according to one selected from the group consisting of (i) a sequential deployment and retrieval and (ii) a simultaneous deployment and retrieval.

In yet another embodiment, the cable of the one or more source feed device includes a Fiber Bragg Grating optical cable. The Fiber Bragg Grating optical cable is configured to implement during a treatment, measuring, via shape-sensing, a location and shape of (a)(i) the at least one radiation source or seed receiving channel and (a)(ii) the radiation source or seed in response to at least one selected from the group including (b)(i) being deployed into the at least one radiation source or seed receiving channel to at least the target region and (b)(ii) being retrieved out of the at least one radiation source or seed receiving channel from at least the target region.

According to a still further embodiment, the at least one radiation source or seed receiving channel comprises an array of channels. The one or more source feed device comprises a plurality of source feed devices. Still further, the plurality of source feed devices are deployed into and retrieved out of the array of channels according to the treatment plan, wherein deployment and retrieval of the plurality of source feed devices include one selected from the group including (c)(i) a sequential deployment and retrieval and (c)(ii) a simultaneous deployment and retrieval.

According to yet another embodiment, the method further comprises determining a treatment plan and verifying, prior to implementing each fraction of the treatment plan, the position of the applicator with respect to the target region. The treatment plan includes a number of fractions, wherein each fraction includes irradiating the target region by deploying and retrieving at least one radiation source or seed into and out of the target region via the at least one radiation source or seed channel. The at least one radiation source or seed traverses a respective channel within the target region according to the treatment plan fraction. Prior to implementing each treatment plan fraction, the position of the applicator is verified with respect to the target region. Responsive to the position of the applicator with respect to the target region being verified to be within a threshold amount, the method proceeds with the treatment plan fraction. Responsive to the position of the applicator with respect to the target region not being verified to be within the threshold amount, the method includes modifying the treatment plan to implement corrective measures.

In one embodiment, modifying the treatment plan includes adaptively adjusting the corresponding fraction and any additional fractions of the brachytherapy treatment plan in accordance with a change in the position of the applicator. In another embodiment, verifying includes measuring, via shape-sensing, the location and shape of the at least one radiation source or seed receiving channel of the applicator.

In a further embodiment, the at least one radiation source or seed channel includes an array of channels, and wherein verifying the position of the applicator includes (a)(i) verifying a respective position of the at least one radiation source or seed channel relative to one another and (a)(ii) verifying a respective position of the at least one radiation source or seed channel relative to the target region. Verifying further includes tracking the position of the applicator relative to the target region and comparing the tracked position to at least one selected from the group including (i) a prior tracking position and (ii) a treatment plan designated tracking position.

In a still further embodiment, the applicator comprises an array of radiation source or seed receiving channels. In this embodiment, tracking by measuring, via shape-sensing, includes measuring the location and shape of a predetermined set of radiation source or seed receiving channels of the array. The method further comprises collecting tracked position information about the array in three-dimension based on tracking the position of the applicator to ensure that no change in placement beyond a threshold amount from a designated placement has occurred from one radiation source or seed receiving channel to another. In addition, the collecting of position information about the array in three-dimension is carried out according to at least one selected from the group including (i) real-time collecting of position information over a period of treatment, and (ii) collecting of position information between fractions of the treatment.

In a further embodiment, the brachytherapy method further comprises measuring, via shape-sensing, a location and shape of a portion of an anatomy proximate the target region, wherein the portion of anatomy is susceptible to an undesired irradiation during a treatment of the target region. Measuring, via shape-sensing, the location and shape of the portion of the anatomy includes deploying a Fiber Bragg Grating optical fiber within the portion of the anatomy that is susceptible to the undesired irradiation. For example, in the instance that the portion of the anatomy comprises a urethra, the FBG optical fiber can be deployed within the urethra to measure, via shape-sensing, the location and shape of the urethra during at least one portion of one or more fractions of a brachytherapy treatment. Accordingly, with knowledge of the location and shape of the urethra, appropriate measures with respect to the treatment plan can be taken so as to provide protection to the urethra from undesired irradiation. In another embodiment, the brachytherapy method further comprises generating the high resolution planning image of the target region in conjunction with the measuring, via shape-sensing, the location and shape of the portion of the anatomy by deploying the Fiber Bragg Grating optical fiber within the portion of the anatomy that is susceptible to the undesired irradiation.

According to yet another embodiment, a brachytherapy method comprises implanting an applicator having at least one radiation source or seed receiving channel in soft tissue adjacent a target region to be irradiated; generating a high resolution planning image of the target region including the applicator, the high resolution planning image for use in determining a treatment plan; tracking a position of the applicator relative to the target region and the treatment plan, wherein tracking includes measuring, via shape-sensing, a location and shape of the at least one radiation source or seed receiving channel, wherein tracking includes deploying and retrieving a Fiber Bragg Grating optical fiber into and out of the target region via the at least one radiation source or seed channel, and acquiring measured location and shape information of the at least one radiation source or seed receiving channel via the Fiber Bragg Grating optical fiber; determining the treatment plan, wherein the treatment plan includes a number of fractions, wherein each fraction includes irradiating the target region by deploying and retrieving at least one radiation source or seed into and out of the target region via the at least one radiation source or seed channel, wherein the at least one radiation source or seed traverses a respective channel within the target region according to the treatment plan fraction; and verifying, at least one selected from the group including (a)(i) prior to implementing a treatment plan fraction and (a)(ii) real-time during a treatment plan fraction, the position of the applicator with respect to the target region, wherein verifying includes tracking by measuring, via shape-sensing, the location and shape of the at least one radiation source or seed receiving channel of the applicator and comparing a result of the verification tracking with at least one selected from the group including (b)(i) a prior tracking position and (b)(ii) a treatment plan designated tracking position.

In one embodiment, a brachytherapy apparatus comprises an applicator having at least one radiation source or seed receiving channel configured for being implanted in soft tissue adjacent a target region to be irradiated; means for generating a high resolution planning image of the target region including the applicator, the high resolution planning image for use in determining a three-dimensional treatment plan; and a tracking device for tracking a position of the applicator relative to the target region and the treatment plan, wherein the tracking device is configured to track the position of the applicator by measuring, via shape-sensing, a location and shape of the at least one radiation source or seed receiving channel.

In another embodiment, the brachytherapy apparatus further comprises a delivery device configured to perform at least one selected from the group including (i) deploying at least one radiation source or seed into the target via the at least one radiation source or seed channel of the applicator and (ii) retrieving the at least one radiation source or seed out of the target region via the at least one radiation source or seed channel of the applicator. The delivery device includes one or more source feed device, wherein the one or more source feed device includes a cable having a radiation source or seed coupled to a tip portion of the cable. The delivery device further includes one or more simulation feed device, the one or more simulation feed device each including a Fiber Bragg Grating optical cable. The Fiber Bragg Grating optical cable is configured to implement the measuring, via shape-sensing, a location and shape of the at least one radiation source or seed receiving channel in response to at least one selected from the group including (i) being deployed into the at least one radiation source or seed receiving channel to at least the target region and (ii) being retrieved out of the at least one radiation source or seed receiving channel from at least the target region. In one embodiment, the delivery device comprises an afterloader device.

In a further embodiment, the cable of the one or more source feed device includes a Fiber Bragg Grating optical cable. The Fiber Bragg Grating optical cable is configured to implement during a treatment, measuring, via shape-sensing, a location and shape of the at least one radiation source or seed receiving channel and the radiation source or seed. The measuring, via shape-sensing, by the Fiber Bragg Grating optical cable is in response to at least one selected from the group including (i) being deployed into the at least one radiation source or seed receiving channel to at least the target region and (ii) being retrieved out of the at least one radiation source or seed receiving channel from at least the target region.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be applied to low dose radiation (LDR) Brachytherapy and the permanent placement of radiation seed sources within a target region. In addition, imaging modalities other than ultrasound (e.g., CT, MR, PET or 3D angio, etc.), or in addition to ultrasound, may be utilized during brachytherapy treatment. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A brachytherapy method, comprising:
  implanting an applicator having at least one radiation source or seed receiving channel in soft tissue adjacent a target region to be irradiated;
  generating a high resolution planning image of the target region including the applicator, the high resolution planning image for use in determining a three-dimensional treatment plan; and
  tracking a position of the applicator relative to the target region and the treatment plan,
    wherein tracking the position includes measuring, exclusively via a shape-sensing optic fiber, a location and shape of the at least one radiation source or seed receiving channel.

2. The method of claim 1, further comprising:
  at least one selected from the group consisting of
    (i) deploying at least one radiation source or seed into the target region via the at least one radiation source or seed channel, and
    (ii) retrieving the at least one radiation source or seed out of the target region via the at least one radiation source or seed channel; and
  wherein the at least one radiation source or seed traverses the channel within the target region according to the treatment plan.

3. The method of claim 2, wherein tracking the position includes:
at least one selected from the group consisting of
(i) deploying the shape-sensing optic fiber into the target region, and
(ii) retrieving the shape-sensing optic fiber out of the target region via the at least one radiation source or seed channel; and
acquiring measured location and shape information of the at least one radiation source or seed receiving channel via the shape-sensing optic fiber.

4. The method of claim 2, wherein deploying and retrieving the at least one radiation source or seed into and out of the target region via the at least one radiation source or seed channel includes using a delivery device configured to deploy and retrieve the at least one radiation source or seed into and out of the target region via the at least one radiation source or seed channel.

5. The method of claim 4,
wherein the delivery device includes one or more source feed device, and
wherein the one or more source feed device includes a cable having a radiation source or seed coupled to a tip of the cable.

6. The method of claim 5,
wherein the delivery device further includes one or more simulation feed device, the one or more simulation feed device including the cable, wherein the cable comprises the shape-sensing optic fiber and
wherein the cable is configured to implement the measuring, exclusively via the shape-sensing optical fiber, the location and shape of the at least one radiation source or seed receiving channel in response to at least one of
(i) being deployed into the at least one radiation source or seed receiving channel to at least the target region, and
(ii) being retrieved through the at least one radiation source or seed receiving channel from at least the target region.

7. The method of claim 6,
wherein the at least one radiation source or seed receiving channel comprises an array of channels,
wherein the one or more simulation feed device comprises a plurality of simulation feed devices, and
wherein the plurality of simulation feed devices are deployed into and retrieved through the array of channels according to one selected from the group consisting of (i) a sequential deployment and retrieval and (ii) a simultaneous deployment and retrieval.

8. The method of claim 5,
wherein the cable of the one or more source feed device comprises the shape-sensing optic fiber, and
wherein the cable is configured to implement during a treatment, measuring, exclusively via the shape-sensing optical fiber, the location and shape of (a)(i) the at least one radiation source or seed receiving channel and (a)(ii) the radiation source or seed in response to at least one selected from the group consisting of
(b)(i) being deployed into the at least one radiation source or seed receiving channel to at least the target region and
(b)(ii) being retrieved out of the at least one radiation source or seed receiving channel from at least the target region.

9. The method of claim 8,
wherein the at least one radiation source or seed receiving channel comprises an array of channels,
wherein the one or more source feed device comprises a plurality of source feed devices,
wherein the plurality of source feed devices are deployed into and retrieved through the array of channels according to the treatment plan, and
wherein deployment and retrieval of the plurality of source feed devices include one selected from the group consisting of (c)(i) a sequential deployment and retrieval and (c)(ii) a simultaneous deployment and retrieval.

10. The method of claim 1, further comprising:
determining the treatment plan,
wherein the treatment plan includes a number of fractions, wherein each fraction includes irradiating the target region by deploying and retrieving at least one radiation source or seed into and out of the target region via the at least one radiation source or seed channel,
wherein the at least one radiation source or seed traverses a respective channel within the target region according to the treatment plan fraction; and
verifying, prior to implementing each treatment plan fraction, the position of the applicator with respect to the target region, and
wherein (i) responsive to the position of the applicator with respect to the target region being verified to be within a threshold amount, then proceeding with the treatment plan fraction, and (ii) responsive to the position of the applicator with respect to the target region not being verified to be within the threshold amount, then modifying the treatment plan to implement corrective measures.

11. The method of claim 10, wherein modifying the treatment plan includes adaptively adjusting the corresponding fraction and any additional fractions of the brachytherapy treatment plan in accordance with a change in the position of the applicator.

12. The method of claim 10, wherein verifying includes measuring, exclusively via the shape-sensing optical fiber, the location and shape of the at least one radiation source or seed receiving channel of the applicator.

13. The method of claim 10,
wherein the at least one radiation source or seed channel includes an array of channels, and
wherein verifying the position of the applicator includes (a)(i) verifying a respective position of the at least one radiation source or seed channel relative to one another and (a)(ii) verifying a respective position of the at least one radiation source or seed channel relative to the target region.

14. The method of claim 13, wherein verifying further includes tracking the position of the applicator relative to the target region and comparing the tracked position to at least one selected from the group consisting of (i) a prior tracking position and (ii) a treatment plan designated tracking position.

15. The method of claim 1, wherein generating the high resolution planning image comprises using one or more selected from the group consisting of ultrasound, CT, MRI, X-ray, PET, and other medical imaging.

16. The method of claim 1, wherein determining the three-dimensional treatment plan includes generating a radiation dose distribution map.

17. The method of claim 1, wherein tracking further includes measuring the location and shape, exclusively via the shape-sensing optical fiber, based on (i) Fiber Bragg Grating or (ii) Rayleigh scattering.

18. The method of claim 1, wherein the applicator comprises an array of radiation source or seed receiving channels.

19. The method of claim 18, wherein tracking by measuring, exclusively via the shape-sensing optical fiber, includes measuring the location and shape of a predetermined set of radiation source or seed receiving channels of the array.

20. The method of claim 18, further comprising:
collecting tracked position information about the array in three-dimensions based on tracking the position of the applicator to ensure that no change in placement beyond a threshold amount from a designated placement has occurred from one radiation source or seed receiving channel to another.

21. The method of claim 20, wherein the collecting of position information about the array in three-dimensions is carried out according to at least one selected from the group consisting of
(i) real-time collecting of position information over a period of treatment, and
(ii) collecting of position information between fractions of the treatment.

22. The method of claim 1, further comprising:
measuring, exclusively via the shape-sensing optical fiber, a location and shape of a portion of an anatomy proximate the target region,
wherein the portion of anatomy is susceptible to an undesired irradiation during a treatment of the target region.

23. The method of claim 22, wherein measuring, exclusively via the shape-sensing optical fiber, the location and shape of the portion of the anatomy includes deploying a shape-sensing optic fiber within the portion of the anatomy that is susceptible to the undesired irradiation.

24. The method of claim 23, further comprising:
generating the high resolution planning image of the target region in conjunction with the measuring, exclusively via the shape-sensing optical fiber, the location and shape of the portion of the anatomy by deploying the shape-sensing optic fiber within the portion of the anatomy that is susceptible to the undesired irradiation.

25. A brachytherapy method comprising:
implanting an applicator having at least one radiation source or seed receiving channel in soft tissue adjacent a target region to be irradiated;
generating a high resolution planning image of the target region including the applicator, the high resolution planning image for use in determining a treatment plan;
tracking a position of the applicator relative to the target region and the treatment plan,
wherein tracking includes measuring, exclusively via a Fiber Bragg Grating optical fiber, a location and shape of the at least one radiation source or seed receiving channel,
wherein tracking includes deploying and retrieving the Fiber Bragg Grating optical fiber into and out of the target region via the at least one radiation source or seed channel, and acquiring measured location and shape information of the at least one radiation source or seed receiving channel via the Fiber Bragg Grating optical fiber;
determining the treatment plan,
wherein the treatment plan includes a number of fractions,
wherein each fraction includes irradiating the target region by deploying and retrieving at least one radiation source or seed into and out of the target region via the at least one radiation source or seed receiving channel,
wherein the at least one radiation source or seed traverses a respective channel within the target region according to the treatment plan fraction; and
verifying, at least one selected from the group consisting of (a)(i) prior to implementing a treatment plan fraction and (a)(ii) real-time during a treatment plan fraction, the position of the applicator with respect to the target region,
wherein verifying includes tracking by measuring, exclusively via the Fiber Bragg Grating optical fiber, the location and shape of the at least one radiation source or seed receiving channel of the applicator and comparing a result of the verification tracking with at least one selected from the group consisting of (b)(i) a prior tracking position and (b)(ii) a treatment plan designated tracking position.

26. A brachytherapy apparatus comprising:
an applicator having at least one radiation source or seed receiving channel configured for being implanted in soft tissue adjacent a target region to be irradiated;
means for generating a high resolution planning image of the target region including the applicator, the high resolution planning image for use in determining a three-dimensional treatment plan; and
a tracking device for tracking a position of the applicator relative to the target region and the treatment plan,
wherein the tracking device is configured to track the position of the applicator by measuring, exclusively via a shape-sensing optic fiber, a location and shape of the at least one radiation source or seed receiving channel.

27. The apparatus of claim 26, further comprising:
a delivery device configured to perform at least one selected from the group consisting of
(i) deploying at least one radiation source or seed into the target region via the at least one radiation source or seed channel of the applicator and
(ii) retrieving the at least one radiation source or seed out of the target region via the at least one radiation source or seed channel of the applicator,
wherein the delivery device includes one or more source feed device,
wherein a one of the one or more source feed device includes a cable having a radiation source or seed coupled to a tip portion of the cable.

28. The apparatus of claim 27,
wherein the delivery device further includes one or more simulation feed device, a one of the one or more simulation feed device including the cable, the cable comprising the shape-sensing optic fiber, and
wherein the cable is configured to implement the measuring, exclusively via the shape-sensing optical fiber, a location and shape of the at least one radiation source or seed receiving channel in response to at least one selected from the group consisting of
(i) being deployed into the at least one radiation source or seed receiving channel to at least the target region and (ii) being retrieved out of the at least one radiation source or seed receiving channel from at least the target region.

29. The apparatus of claim 27, wherein the delivery device comprises an afterloader device.

30. The apparatus of claim 27,
wherein the cable of a one of the one or more source feed device includes a shape-sensing sensing optic fiber,
wherein the cable of the one of the one or more source feed device is configured to implement during a treatment, measuring, exclusively via the shape-sensing optic fiber, a location and shape of the at least one radiation source or seed receiving channel and the radiation source or seed in response to at least one selected from the group consisting of
  (i) being deployed into the at least one radiation source or seed receiving channel to at least the target region and
  (ii) being retrieved out of the at least one radiation source or seed receiving channel from at least the target region.

* * * * *